US012800579B2

(12) United States Patent
Kawasaki et al.

(10) Patent No.: US 12,800,579 B2
(45) Date of Patent: Nov. 17, 2026

(54) IMMUNOCHROMATOGRAPHY MEASUREMENT METHOD, AUXILIARY LIQUID FOR IMMUNOCHROMATOGRAPHY MEASUREMENT, IMMUNOCHROMATOGRAPHY CHIP, AND IMMUNOCHROMATOGRAPHY MEASUREMENT KIT

(71) Applicant: NATIONAL UNIVERSITY CORPORATION HAMAMATSU UNIVERSITY SCHOOL OF MEDICINE, Hamamatsu (JP)

(72) Inventors: Hideya Kawasaki, Hamamatsu (JP); Takahiko Hariyama, Hamamatsu (JP)

(73) Assignee: NATIONAL UNIVERSITY CORPORATION HAMAMATSU UNIVERSITY SCHOOL OF MEDICINE, Shizuoka (JP)

( * ) Notice: Subject to any disclaimer, the term of this patent is extended or adjusted under 35 U.S.C. 154(b) by 831 days.

(21) Appl. No.: 17/920,884

(22) PCT Filed: Apr. 8, 2021

(86) PCT No.: PCT/JP2021/014841
§ 371 (c)(1),
(2) Date: Oct. 24, 2022

(87) PCT Pub. No.: WO2021/220755
PCT Pub. Date: Nov. 4, 2021

(65) Prior Publication Data

US 2023/0258632 A1 Aug. 17, 2023

(30) Foreign Application Priority Data

Apr. 30, 2020 (JP) ................................ 2020-079912

(51) Int. Cl.
*G01N 33/543* (2006.01)
*G01N 23/2252* (2018.01)
*G01N 33/569* (2006.01)

(52) U.S. Cl.
CPC ... *G01N 33/54387* (2021.08); *G01N 23/2252* (2013.01); *G01N 33/56983* (2013.01);
(Continued)

(58) Field of Classification Search
None
See application file for complete search history.

(56) References Cited

U.S. PATENT DOCUMENTS

2007/0059763 A1 3/2007 Okano et al.
2008/0206889 A1 * 8/2008 Harris .............. G01N 33/54313
436/518
(Continued)

FOREIGN PATENT DOCUMENTS

JP 2000-338106 12/2000
JP 2006-112792 4/2006
(Continued)

OTHER PUBLICATIONS

Notice of Reasons for Refusal dated Dec. 3, 2024 in corresponding Japanese Patent Application No. 2022-517593, with English-language translation.
(Continued)

*Primary Examiner* — Rebecca M Giere
(74) *Attorney, Agent, or Firm* — Wenderoth, Lind & Ponack, L.L.P.

(57) ABSTRACT

The present invention provides a highly sensitive immunochromatography measurement method in which a labeling substance for labeling an object to be detected in a specimen undergoing immunochromatography is quantified by being identified with precision, high resolution, and increased
(Continued)

contrast using an electron microscope. An immunochromatography measurement method according to an embodiment of the present invention is characterized in that measurement is performed by an electron microscope after applying an auxiliary liquid other than a specimen in the immunochromatography.

18 Claims, 10 Drawing Sheets

(52) U.S. Cl.
CPC .... *G01N 2223/418* (2013.01); *G01N 2333/11* (2013.01); *G01N 2469/10* (2013.01)

(56) References Cited

U.S. PATENT DOCUMENTS

| | | | | |
|---|---|---|---|---|
| 2009/0111196 | A1 | 4/2009 | Oyamada et al. | |
| 2011/0053289 | A1* | 3/2011 | Lowe | G01N 33/54326 436/501 |
| 2016/0257959 | A1* | 9/2016 | Alsager | G01N 33/5308 |
| 2016/0343539 | A1 | 11/2016 | Hariyama et al. | |

FOREIGN PATENT DOCUMENTS

| | | |
|---|---|---|
| JP | 2009-98139 | 5/2009 |
| JP | 2009-192224 | 8/2009 |
| JP | 2017-201289 | 11/2017 |
| JP | 2020-153960 | 9/2020 |

OTHER PUBLICATIONS

Extended European Search Report issued Apr. 26, 2024 in corresponding European Patent Application No. 21796894.0.

Y. Takaku et al., “A thin polymer membrane, nano-suit, enhancing survival across the continuum between air and high vacuum”, Proceedings of the National Academy of Sciences, vol. 110, No. 19, Apr. 15, 2013, pp. 7631-7635.

D. Quesada-González et al., “Signal enhancement on gold nanoparticle-based lateral flow tests using cellulose nanofibers”, Biosensors and Bioelectronics, Elsevier Science Ltd, vol. 141, Jun. 7, 2019.

K. Shinmura et al., “Utility of Scanning Electron Microscopy Elemental Analysis Using the ‘NanoSuit’ Correlative Light and Electron Microscopy Method in the Diagnosis of Lanthanum Phosphate Deposition in the Esophagogastroduodenal, Mucosa”, Diagnostics, vol. 10, No. 1, Dec 18, 2019, p. 1-11.

International Search Report issued Jun. 8, 2021 in International (PCT) Application No. PCT/JP2021/014841.

Kawasaki et al., “High sensitive quantitative and rapid immunochromatographic diagnosis of the clinical samples using scanning electron microscopy—preparing for future outbreaks,” med Rxiv, May 20, 2020, 16 pages.

Kawasaki et al., “Combination of the NanoSuit method and gold/platinum particle-based lateral flow assay for quantitative and highly sensitive diagnosis using a desktop scanning electron microscope”, Journal of Pharmaceutical and Biomedical Analysis, Jan. 26, 2021, vol. 196, Article No. 113924.

* cited by examiner (a)

(b)

(a)

(b)

(a)

(b)

(a)

(b)

(a)

(b)

(a)

(b)

IMMUNOCHROMATOGRAPHY MEASUREMENT METHOD, AUXILIARY LIQUID FOR IMMUNOCHROMATOGRAPHY MEASUREMENT, IMMUNOCHROMATOGRAPHY CHIP, AND IMMUNOCHROMATOGRAPHY MEASUREMENT KIT

TECHNICAL FIELD

The present invention relates to an immunochromatography measurement method, an auxiliary liquid for immunochromatography measurement, an immunochromatography chip, and an immunochromatography measurement kit.

BACKGROUND ART

To prevent the spread of infectious diseases by pathogens such as bacteria and viruses, early detection and treatment of infections is important, and pathogens require highly sensitive detection. Conventionally, a culture methods, a PCR method, a LAMP method, an ELISA method, immunochromatography, and the like have been used to definitively diagnose infectious diseases.

The culture method requires a long time to determine results, and only a pathogen predicted in advance can be detected. With the PCR method also, only a pathogen predicted in advance can be detected, and further, a negative determination does not necessarily negate the presence of the pathogen. While the PCR method is a method allowing highly sensitive detection due to repeating DNA amplification, since it is necessary to repeat the amplification reaction, there is also a risk of causing an erroneous positive determination due to contamination from a positive control or the like. In addition, the PCR method is more complicated in terms of operation and requires a longer time for determination (about 5 to 6 hours) when compared to immunochromatography. With the LAMP method (loop-mediated isothermal amplification), DNA amplification reaction to detection can be performed in a one-step process due to a primer design that differs from the PCR method, however, in the same way as the PCR method, operation of the LAMP method is more complicated when compared to immunochromatography. The ELISA method can detect a pathogen (an antigen) in a specimen using an antibody against the pathogen and is faster than the PCR method and the LAMP method, however it may cause an erroneous positive determination due to a non-specific antigen-antibody reaction or the like. There remains a risk that any of these techniques may lead to a false positive or a false negative result.

Immunochromatography is currently implemented in society as a diagnostic aid for various diseases, primarily influenza viruses. A principle thereof is one that uses the antigen-antibody reaction, and its simplicity and effectiveness means that the method is widely used in medical practice. A problem of immunochromatography is that sensitivity is not as high as in the PCR method, and the presence or absence of infection cannot be diagnosed unless the virus (pathogen) has proliferated in a patient's body to some extent. In addition, with immunochromatography, it is possible to determine whether a sample is positive or negative with the naked eye, however a disadvantage is that it is difficult to quantify the results (for example, measuring a quantity of viruses).

Various methods have been proposed up to present to compensate for the above-described problem and disadvantage of immunochromatography. For example, in a case of a system having a small densitometry analyzer combined with immunochromatography, it is possible to perform quantification using densitometry, however measurement sensitivity of a detection unit (a test line) is often poor, and it is difficult to increase sensitivity. It has also been reported that using densitometry may not be appropriate depending on the kind of specimen (see Patent Literature 1).

Patent Literature 2 proposes that a gold labeled signal is amplified using fine gold particles including a predetermined amount of silver as a labeling material for detection. While increasing sensitivity by silver sensitization such as is disclosed in Patent Literature 2 leads to higher sensitivity when compared to conventional methods, since the invention undergoes a step of silver sensitization, there is such instability that a result determination depends on a sensitization reaction. In addition, amplification of the signal following the sensitization step not limited to silver simply means making the antigen-antibody reaction on an immunochromatography chip easier to be confirmed with the naked eye, and an increase in sensitivity to the extent expected upon actual use has not been achieved.

CITATION LIST

Patent Literature

Patent Literature 1: JP 2000-338106 A
Patent Literature 2: JP 2009-192224 A

SUMMARY OF INVENTION

Technical Problem

In view of the above circumstances, an object of the present invention is to provide a highly sensitive immunochromatography measurement method in which a labeling substance for labeling an object to be detected in a specimen undergoing immunochromatography is quantified by being identified with precision, high resolution, and increased contrast using an electron microscope.

In addition, another object of the present invention is to provide an auxiliary liquid for immunochromatography measurement to be used for measuring an immunochromatography chip by the electron microscope.

A further object of the present invention is to provide an immunochromatography chip to be used in the above immunochromatography measurement method.

Moreover, another object of the present invention is to provide an immunochromatography measurement kit including the above auxiliary liquid as a constituent element, and further including the above immunochromatography chip as a constituent element as necessary.

Solution to Problem

Currently, for many immunochromatography chips generally in use, a labeled antibody in which a labeling substance is bound to an antibody against an object to be detected and a capture antibody for identifying an epitope different from the labeled antibody is used to form an antigen-antibody reaction product consisting of a labeled antibody-object to be detected (antigen)-capture antibody, and color development caused by accumulation of the labeling substance bound to the labeled antibody is confirmed with the naked eye or the like. The present inventors have found that when a detection unit of this kind of immunochromatography chip is subjected to measurement by electron microscope, as shown as Comparative Example 1 in the later-described examples, images are unclear, thus it is difficult to clearly distinguish a carrier on which the capture antibody is immobilized (for example, a nitrocellulose membrane) and the antigen-antibody reaction product on the carrier (the labeling substance) in the images. This is believed to be due to the carrier and the antigen-antibody reaction product being charged by a continuous electron beam irradiation from an electron source of the electron microscope to generate heat in the carrier and the antigen-antibody reaction product and destabilizing these through a generated structural change, causing loss in sharpness of the images.

Therefore, the present inventors conceived of applying an auxiliary liquid other than a specimen to structurally stabilize a sample (an object to be detected) under measurement conditions by electron microscope and improve sharpness of electron microscope images (obtain high contrast electron microscope images), and as a result of intensive studies, arrived at completing the present invention.

In other words, the present invention includes the following aspects.

(1) An immunochromatography measurement method in which measurement is performed by an electron microscope after applying an auxiliary liquid other than a specimen undergoing immunochromatography.

(2) The method according to (1), in which the auxiliary liquid is provided with conductivity for preventing charging and heat generation, which contributes to sharpness of images under measurement conditions by electron microscope.

(3) The method according to (1) or (2), in which the auxiliary liquid has a property of forming a membrane by polymerization under the measurement conditions by electron microscope.

(4) The method according to any one of (1) to (3), in which the method is immunochromatography using a labeled antibody supporting metal nanoparticles as a labeling substance, and a capture antibody having a property of binding to a complex of the labeled antibody and an object to be detected.

(5) The method according to (4), in which the capture antibody is immobilized on an immunochromatography chip at intervals.

(6) The method according to any one of (1) to (5), in which the specimen and the auxiliary liquid are applied simultaneously.

(7) The method according to any one of (1) to (5), in which the auxiliary liquid is developed after the specimen has been developed.

(8) The method according to any one of (1) to (7), in which the object to be detected is identified by identifying the labeling substance in electron microscope images using artificial intelligence.

(9) The method according to any one of (1) to (7), in which the object to be detected is identified by identifying the labeling substance in the electron microscope images using energy dispersive X-ray spectroscopy (EDX).

(10) An auxiliary liquid for immunochromatography measurement for improving sharpness of images when measuring an immunochromatography chip by an electron microscope.

(11) The auxiliary liquid according to (10), having a property of being conductive under measurement conditions by electron microscope.

(12) The auxiliary liquid according to (10) or (11), having a property of forming a membrane by polymerization under measurement conditions by electron microscope.

(13) The auxiliary liquid according to any one of (10) to (12), including at least one compound selected from the group consisting of glycerin, a glycerin substitute, polysorbates such as polysorbate 20, polysorbate 40, polysorbate 60, polysorbate 65, polysorbate 80, and polysorbate 85, and a polysorbate alternative as an essential component; and including at least one compound selected from monosaccharides, disaccharides, salts, and a buffer solution as an optional component.

(14) An immunochromatography chip to be used in the method according to any one of (1) to (9), in which the chip is provided with a detection unit dedicated to electron microscope measurement.

(15) The immunochromatography chip according to (14), in which a labeled antibody supporting metal nanoparticles as a labeling substance is immobilized at a predetermined position, and a capture antibody having a property of binding to a complex of the labeled antibody and an object to be detected is immobilized on the detection unit dedicated to electron microscope measurement.

(16) The immunochromatography chip according to (15), in which the capture antibody is immobilized at intervals.

(17) The immunochromatography chip according to any one of (14) to (16), further provided with a detection unit for visual observation.

(18) The immunochromatography chip according to any one of (14) to (16), not provided with any detection units other than the detection unit dedicated to electron microscope measurement.

(19) An immunochromatography measurement kit including the auxiliary liquid according to any one of (10) to (13) as a constituent element.

(20) The kit according to (19), further including the immunochromatography chip according to any one of (14) to (18) as a constituent element.

Advantageous Effects of Invention

According to the present invention, a highly sensitive immunochromatography measurement method is provided in which a labeling substance for labeling an object to be detected in a specimen undergoing immunochromatography is quantified by being identified with precision, high resolution, and increased contrast using an electron microscope. Specifically, in the method of the present invention, since by applying an auxiliary liquid other than the specimen, a contrast between a background carrier and a target object to be detected is clear and the labeling substance of the object to be detected can be identified as clear (well-defined) particles when measuring an immunochromatography chip by the electron microscope, the results of immunochromatography can be easily quantified in a short time by measuring a quantity of the labeling substance. In one aspect of the method of the present invention, the above-described effect can be efficiently obtained by the above auxiliary liquid being provided with conductivity for preventing charging and heat generation, which contributes to sharpness of images, and/or having a property of forming a membrane by polymerization, under measurement conditions by electron microscope. In the method of the present invention, since the object to be detected on the chip can be identified at high magnification and high resolution using an electron microscope, increased sensitivity is possible at a degree of about 10 times to 100 times in comparison to a conventional qualitative determination using visual observation. In other words, in the method of the present invention, even when a concentration of the object to be detected in the specimen is 10 times to 100 times lower in comparison to a conventional specimen, the object to be detected can be identified by subjecting the immunochromatography chip to measurement by electron microscope to identify the labeling substance of the object to be detected.

In addition, according to the present invention, an auxiliary liquid for immunochromatography measurement to be used for measurement of the immunochromatography chip by the electron microscope is provided. Specifically, the auxiliary liquid for immunochromatography measurement of the present invention improves the sharpness of the electron microscope images of the immunochromatography chip, and by applying the auxiliary liquid of the present invention, it is possible to obtain high contrast images when measuring the immunochromatography chip by the electron microscope. In one aspect of the auxiliary liquid of the present invention, the above-described effect can be efficiently obtained by the auxiliary liquid having a property of conductivity under measurement conditions by electron microscope, and/or having a property of forming a membrane by polymerization.

In addition, according to the present invention, the immunochromatography chip to be used in the above immunochromatography measurement method is provided. Specifically, the immunochromatography chip of the present invention is provided with a detection unit dedicated to electron microscope measurement. In the immunochromatography chip of the present invention, since highly magnified and high-resolution images are obtained in the detection unit dedicated to electron microscope measurement under measurement conditions by the electron microscope, detection units other than the detection unit in question are not necessarily required. In other words, in an aspect in which only the detection unit dedicated to electron microscope measurement is provided as the detection unit, by subjecting the immunochromatography chip on which a specimen has been developed to measurement by electron microscope, a quantified result can be obtained quickly and more easily. Meanwhile, in another aspect of the immunochromatography chip of the present invention, a detection unit for visual observation is further provided in addition to the detection unit dedicated to electron microscope measurement, and through this, screening by visual observation and measurement by electron microscope can be performed by separate detection units. In other words, it is possible to perform a two-step detection which involves, as a first step, performing a simple screening by confirming, by visual observation, color development originating from the labeling substance for labeling the object to be detected on the detection unit for visual observation, then, as a second step, quantifying by measuring a quantity of the labeling substance on the detection unit dedicated to electron microscope measurement by performing measurement by the electron microscope. The effects obtained by these aspects will be described in detail below.

In addition, according to the present invention, a highly sensitive immunochromatography measurement kit is provided in which the labeling substance for labeling an object to be detected in a specimen undergoing immunochromatography is quantified by being identified with precision, high resolution, and increased contrast using the electron microscope. Specifically, the kit of the present invention includes the above auxiliary liquid for immunochromatography measurement as a constituent element. Further, the kit of the present invention may further include the above immunochromatography chip as a constituent element as necessary. In the kit of the present invention, for example, the labeling substance for labeling the object to be detected in the specimen can be identified with precision, high resolution, and increased contrast by using metal nanoparticles such as gold nanoparticles, and platinum-gold nanoparticles, which have been used in conventional immunochromatography as a labeling substance, in combination with a scanning electron microscope (SEM) as a signal, and the results of immunochromatography can be easily quantified in a short time by measuring a quantity of metal nanoparticles. In addition, the kit can be utilized as a diagnosis aid for various diseases by comparing the quantified data with background data and establishing determination criteria such as setting a significant difference (for example, a p-value by t-test is $p<0.01$ or less) as positive. Note that when the kit of the present invention is used in combination with a SEM, the SEM is not limited to a specific model, and a wide range of models, from an FE-SEM to a tabletop SEM, can be used.

DESCRIPTION OF EMBODIMENTS

Figure 1:
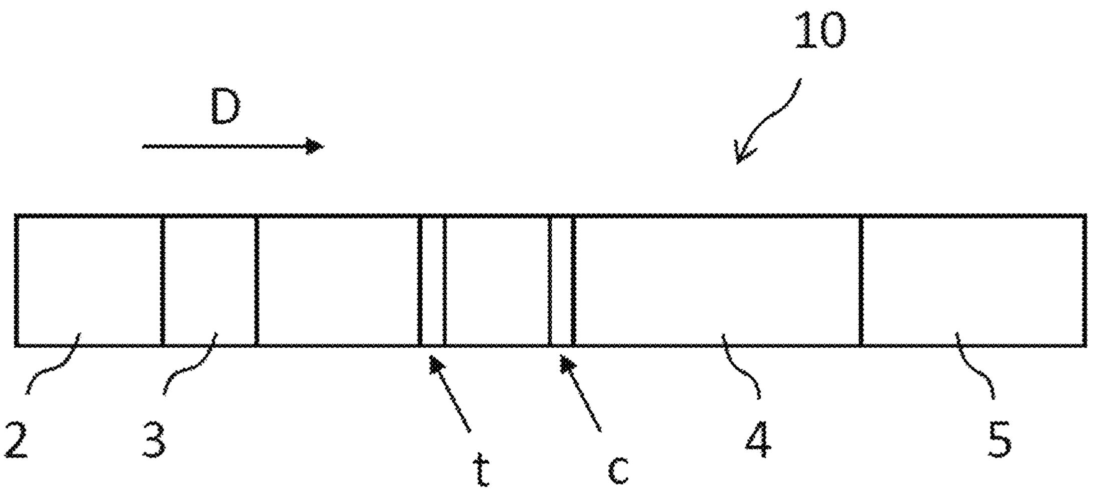
FIG. 1 is a schematic plan view showing an example of a configuration of an immunochromatography chip that can be used in the method of the present invention.

The embodiments of the present invention will be described in detail below. Note that specific modalities are not limited to the following embodiments, and any modification in design or the like in a scope that does not depart from the gist of the present invention is also included in the present invention.

<Immunochromatography Measurement Method>

The immunochromatography measurement method of the present invention (hereinafter also referred to as simply the "method of the present invention") is characterized in that measurement is performed by an electron microscope after applying an auxiliary liquid other than a specimen undergoing immunochromatography (hereinafter also referred to as an "auxiliary liquid for immunochromatography measurement").

[Auxiliary Liquid for Immunochromatography Measurement]

The auxiliary liquid for immunochromatography measurement (hereinafter also referred to as simply an "auxiliary liquid") is preferably provided with conductivity for preventing charging and heat generation, which contributes to sharpness of electron microscope images, and/or has a property of forming a membrane by polymerization. In addition, it is preferable that the auxiliary liquid can wash away contaminants on an entire carrier 4 including a detection unit t, a control unit c, and the like of an immunochromatography chip 10 to be illustratively described below with reference to FIGS. 1 and 2 and allow a labeling substance on the detection unit t and the control unit c to be clarified under measurement conditions by electron microscope. By providing an auxiliary liquid with at least one or more, and more preferably all of these characteristics, a contrast between a background carrier (for example, a nitrocellulose membrane) and a target object to be detected becomes clear, instability of a background caused by swelling or the like due to heat generation is removed, and a labeling substance of the object to be detected (for example, metal nanoparticles such as gold nanoparticles, and platinum-gold nanoparticles) can be identified as clear (well-defined) particles when measuring the immunochromatography chip by the electron microscope, therefore the results of immunochromatography can be easily quantified in a short time by measuring a quantity of these labeling substances.

In other words, the auxiliary liquid for immunochromatography measurement of the present invention improves the sharpness of the images when measuring the immunochromatography chip by the electron microscope. The auxiliary liquid of the present invention preferably has a property of conductivity and/or a property of forming a membrane by polymerization under measurement conditions by electron microscope. More specifically, the auxiliary liquid of the present invention includes at least one compound selected from the group consisting of glycerin, a glycerin substitute, polysorbates such as polysorbate 20, polysorbate 40, polysorbate 60, polysorbate 65, polysorbate 80, and polysorbate 85, and a polysorbate alternative as an essential component; and includes at least one compound selected from monosaccharides, disaccharides, salts, and a buffer solution as an optional component.

The glycerin is a trihydric alcohol (a so-called polyhydric alcohol), which has a hydroxyl group in the molecule and is a low vapor pressure substance. In addition, the glycerin has viscosity. A substance having these characteristics can be included in the auxiliary liquid of the present invention as a substitute component for the glycerin. Specifically, examples of the glycerin substitute include polyethylene glycol, polyvinyl alcohol, triglyceride, polyresorcinol, polyphenol, tannic acid, urushiol, saponin, and the like. One kind of the glycerin and the glycerin substitute may be used alone, or two or more kinds may be used in combination.

In the present specification, "polysorbates" refer to those prepared by reacting ethylene oxide with a sorbitan fatty acid ester (a nonionic surfactant). Polysorbates currently generally available include polysorbate 20 (Tween 20), polysorbate 40 (Tween 40), polysorbate 60 (Tween 60), polysorbate 65 (Tween 65), polysorbate 80 (Tween 80), and polysorbate 85 (Tween 85), however the polysorbates that can be included in the auxiliary liquid of the present invention are not limited hereto. In addition, in the same way as the polysorbates, substances classified as nonionic surfactants can be included in the auxiliary liquid of the present invention as a substitute component of the polysorbates. Specifically, examples of the polysorbate substitute include polyoxyethylene alkyl ether, polyoxyethylene hydrogenated castor oil, polyoxyethylene mono fatty acid ester, sucrose fatty acid ester, polyglycerin fatty acid ester, alkyl polyglycoside, N-methyl alkyl glucamide, and the like. One kind of the polysorbate and the polysorbate substitute may be used alone, or two or more kinds may be used in combination.

Examples of the monosaccharide include glucose, fructose, and the like.

Examples of the disaccharide include sucrose, trehalose, and the like.

Examples of the salt include imidazolium salts, pyridinium salts, piperidinium salts, pyrrolidinium salts, quaternary ammonium salts, and the like.

Examples of the buffer solution include an acetate buffer solution (an acetate/sodium acetate buffer solution), a phosphate buffer solution (a phosphate/sodium phosphate buffer solution), a citrate buffer solution (a citrate/sodium citrate buffer solution), a citrate phosphate buffer solution (a citrate/ sodium phosphate buffer solution), a borate buffer solution, a tartrate buffer solution, a Tris buffer solution, and the like.

One kind of these monosaccharides, disaccharides, salts, and buffer solutions may be used alone, or two or more kinds may be used in combination.

The essential component consisting of at least one compound selected from glycerin, a glycerin substitute, polysorbates, and a polysorbate substitute is preferably contained in the auxiliary liquid at 0.01 weight percent to 10 weight percent, and more preferably contained at 0.1 weight percent to 2 weight percent.

[Immunochromatography]

In the method of the present invention, the principles of immunochromatography and detection method for the object to be detected are not particularly limited. Note that while the invention will be described below with the example of immunochromatography using a labeled antibody supporting metal nanoparticles as a labeling substance and a capture antibody having a property of binding to a complex of the labeled antibody and the object to be detected given as a representative embodiment of the method of the present invention, it should be noted that specific aspects of the immunochromatography in the method of the present invention are not limited hereto.

In the present embodiment, the "object to be detected" is a substance having a property of specifically identifying and binding to the above labeled antibody and capture antibody; that is, antigenicity. In other words, in the present embodiment, the object to be detected is an antigen. The antigen may have or may not have immunogenicity. Note that in the latter case, the object to be detected is also called a hapten or incomplete antigen.

Examples of the antigen include a pathogen such as viruses, viroids, bacteria, and fungi; an extracellular endoplasmic reticulum such as exosomes, microvesicles, and apoptotic bodies; a protein, DNA, or RNA originating from a body fluid (blood, serum, saliva, urine, or the like) or hair of a test animal; a protein, DNA, or RNA originating from an organ, a tissue, or a cell of a test plant; a heavy metal such as mercury, arsenic, aluminum, cadmium, lead, nickel, and tin; and allergens such as tree or plant pollen, mites, house dust, and food (eggs, wheat, or the like), however they are not limited hereto. Among these, since the method of the present invention involves performing measurement by electron microscope, it is suitable for cases in which measurement by an optical microscope is not possible, such as for viruses, and viroids.

The virus may be a DNA virus, or it may be an RNA virus.

Examples of the DNA virus include Poxviridae (variola (small pox) virus, monkeypox virus, and the like), Herpesviridae (herpes simplex virus, varicella zoster virus, cytomegalovirus, Epstein-Barr virus, and the like), Adenoviridae (adenovirus), Papovaviridae (papillomavirus, JC virus, and the like), Parvoviridae (parvovirus), and Hepadnaviridae (hepatitis B virus and the like).

Examples of the RNA virus include Arenaviridae (Lassa virus and the like), Orthomyxoviridae (influenza virus and the like), Caliciviridae (norovirus, sapovirus, and the like), Coronaviridae (SARS virus, MERS virus, and the like), Togaviridae (rubella virus and the like), Nodaviridae (viral neuro necrosis virus and the like), Paramyxoviridae (mumps virus, measles morbillivirus, respiratory syncytial (RS) virus, and the like), Picornaviridae (poliovirus, coxsackievirus, echovirus, and the like), Filoviridae (Marburg virus, Ebolavirus, and the like), Bunyaviridae (Crimean-Congo hemorrhagic fever virus, severe fever with thrombocytopenia syndrome (SFTS) virus, and the like), Flaviviridae (yellow fever virus, dengue virus, hepatitis C virus, hepatitis G virus, and the like), Rhabdoviridae (rabies virus and the like), Reoviridae, and Retroviridae (human immunodeficiency virus, human T-cell lymphotropic virus, simian immunodeficiency virus, simian-T-lymphotropic virus (STLV), and the like).

Examples of the viroid include Absanviridae and Pospiviridae.

Examples of the bacteria include *Staphylococcus, Escherichia coli, Salmonella, Pseudomonas aeruginosa, Vibrio cholerae, Shigella, Bacillus anthracis, Mycobacterium tuberculosis, Clostridium botulinum, Clostridium tetani, Streptococcus*, and the like.

Examples of the fungi include *Trichophyton, Candida*, and *Aspergillus*.

Note that the above-described viruses, viroids, bacteria, and fungi may be known, or they may be unknown.

[Immunochromatography Chip]

Figure 2:
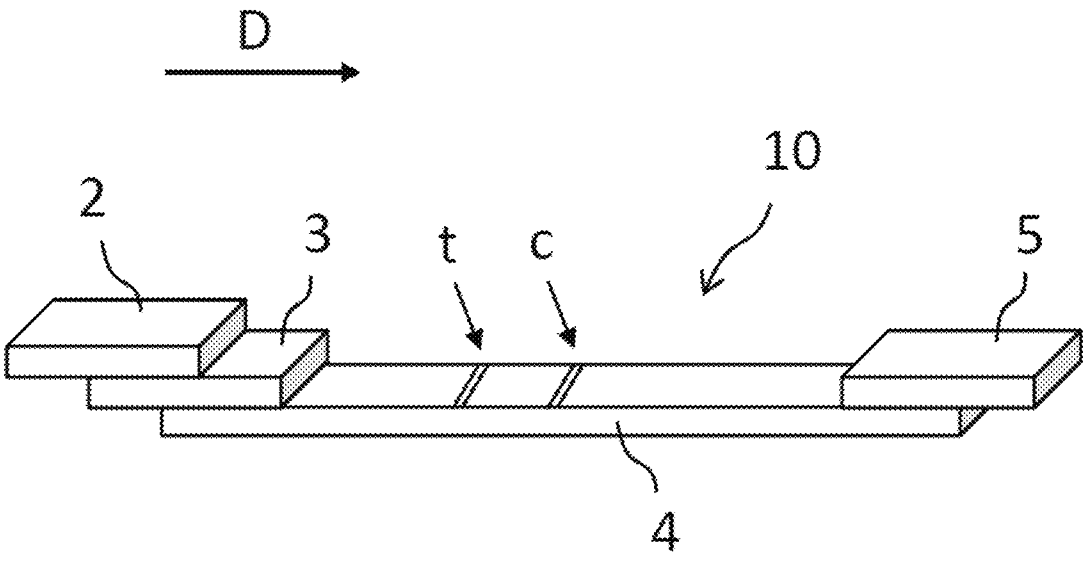
FIG. 2 is a schematic perspective view showing an example of a configuration of an immunochromatography chip that can be used in the method of the present invention.

FIGS. 1 and 2 are, respectively, a schematic plan view and a perspective view showing an example of a configuration of an immunochromatography chip (also referred to as a development support body, a chromatographic medium, and the like) that can be used in the method of the present invention. Note that the immunochromatography chip that can be used in the method of the present invention is not particularly limited to one having the configuration shown in FIGS. 1 and 2, as long as it is a chip that can be used in ordinary immunochromatography.

A chip 10 shown in FIGS. 1 and 2 is provided with a specimen pad 2, a conjugate pad 3, a carrier 4, and an absorbent pad 5 from upstream to downstream in a development direction (the direction shown by an arrow D in FIGS. 1 and 2). These members are fixed on a base material (also referred to as a backing sheet or the like; not shown) by an adhesive agent, an adhesive sheet, or the like. Note that a transparent film (not shown) or the like may be applied to an upper surface of the carrier 4, and a functional sheet or the like may be provided between each member.

The specimen is dropped on the specimen pad 2. For example, a glass fiber pad, a cellulose fiber pad, a polyester pad, or the like can be used as the specimen pad 2.

A labeled antibody in which a labeling substance is bound to an antibody against the object to be detected is immobilized on the conjugate pad 3. The conjugate pad 3 can be prepared, for example, by preparing a suspension containing the above labeled antibody and applying the suspension to a suitable absorbent pad (for example, a glass fiber pad, a cellulose fiber pad, a polyester pad, or the like), then drying the pad. A labeling substance used in conventional immunochromatography can be used as the labeling substance. For example, coloring fine particles such as metal nanoparticles (metal fine particles), latex fine particles, organic polymer fine particles, inorganic fine particles, and liposomes containing a color forming agent can be used. More specifically, examples of the metal nanoparticles include noble metal nanoparticles such as gold nanoparticles, platinum nanoparticles, platinum-gold nanoparticles, and silver nanoparticles; titanium nanoparticles; iron nanoparticles; nickel nanoparticles; and cadmium nanoparticles. Note that the metal nanoparticles may be colloidal metal nanoparticles having a particle size of 1 nm to 100 nm.

A material used in conventional immunochromatography can be used as the carrier 4, and, for example, a nitrocellulose membrane or the like can be used. The carrier 4 includes a detection unit t and a control unit c. A capture antibody having a property of identifying an epitope different from the labeled antibody immobilized on the conjugate pad 3 and binding to the complex of the labeled antibody and the object to be detected is immobilized on the detection unit t. An antibody (also called a control antibody) for specifically identifying the labeled antibody immobilized on the conjugate pad 3 is immobilized on the control unit t. Note that in FIGS. 1 and 2, the ranges of the detection unit t and the control unit c are shown as a solid line for the sake of clarity, however it is not intended that a line or the like showing a boundary between the detection unit t and the control unit c is provided on a chip actually being used.

The absorbent pad 5 plays the role of absorbing excess specimen or the like after developing using chromatography. For example, a glass fiber pad, a cellulose fiber pad, a polyester pad, or the like can be used as the absorbent pad 5.

The object to be detected in the specimen dropped on the specimen pad 2 reacts with the labeled antibody immobilized on the conjugate pad 3 to form a complex. This complex develops on the carrier 4 and is captured by the capture antibody immobilized on the detection unit t of the carrier 4, and through this, color development, which originates from the labeling substance of the labeled antibody accumulated on the detection unit t, occurs. In addition, excess labeled antibody is captured by the control antibody immobilized on the control unit c of the carrier 4, and through this, the color development, which originates from the labeling substance of the labeled antibody accumulated in the control unit c, occurs. Also, the excess specimen developed downstream of the control unit c of the carrier 4 is absorbed by the absorbent pad 5.

Figure 3:
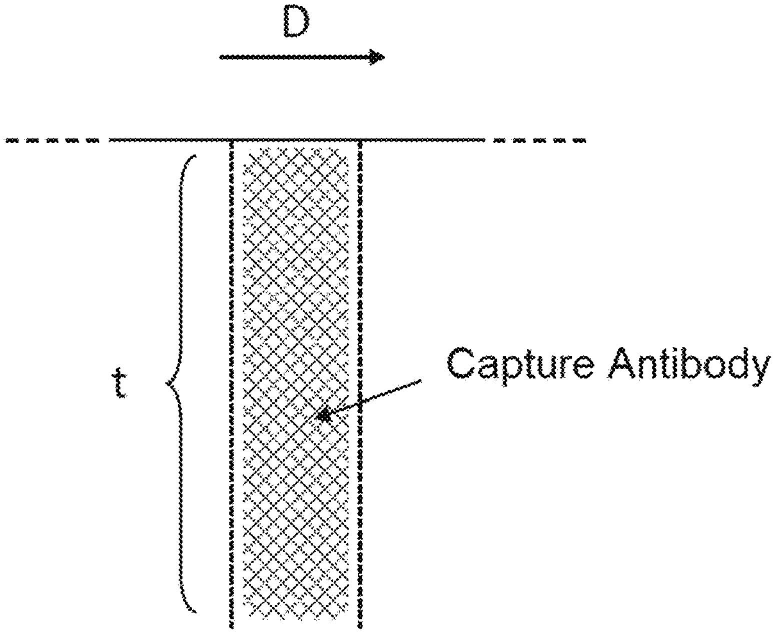
FIG. 3 is a schematic plan view showing examples of aspects of a detection unit of the immunochromatography chip shown in FIGS. 1 and 2; (a) is an aspect in which a capture antibody is immobilized in a line, and (b) is an aspect in which a range over which a capture antibody is immobilized is smaller than that of the aspect shown in (a).
Figure 3:
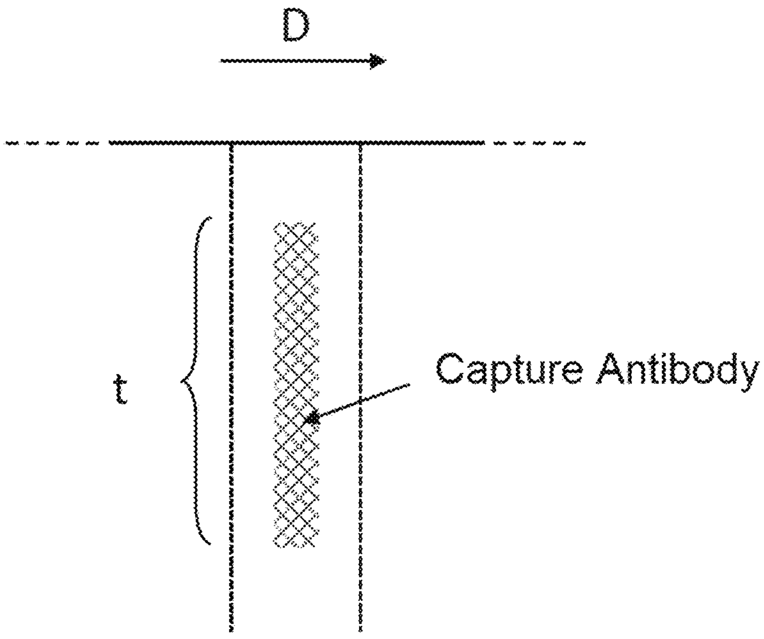

Note that in a conventional immunochromatography chip, a capture antibody and a control antibody are normally respectively immobilized in lines in a direction perpendicular to a development direction (that is, in parallel to a shorter edge of a carrier). Accordingly, a detection unit and a control unit are also respectively referred to as a detection line (a test line) and a control line. FIG. 3(*a*) is an illustration schematically showing a case in which the detection unit t of the chip 10 shown in FIGS. 1 and 2 is this aspect.

On the other hand, as described in detail below, according to the method of the present invention, since the labeling substance for labeling the object to be detected in the specimen can be identified with precision, high resolution, and increased contrast using an electron microscope, the ranges of the detection unit and the control unit can be reduced to less than that of a conventional immunochromatography chip, which is premised on confirmation by visual observation. FIG. 3(*b*) is an illustration schematically showing an aspect in which the range over which the capture antibody is immobilized is smaller than that of the aspect of the detection unit t shown in FIG. 3(*a*). In other words, in the present aspect, an amount of the capture antibody used can be reduced to less than that of the aspect shown in FIG. 3(*a*), and consequently, an amount of the specimen can be reduced. Alternatively, it is also possible to increase an antibody concentration on the detection unit t, that is, an amount of antibody per unit area of the detection unit t, by immobilizing a same amount of capture antibody as conventional techniques over a smaller range. Naturally, even when the amount of capture antibody used is reduced to less than that of conventional techniques, it is possible to increase the antibody concentration on the detection unit t. Note that while it is not shown in FIG. 3(*b*), the same applies to the control unit c. The small range of the detection unit t and the control unit c means that selecting a measurement site (measurement position) of the detection unit t or the control unit c, work to align the measurement site (measurement position) with a field of view of the electron microscope, and the like can be more easily performed when measuring by electron microscope, thus the effects of improving a measurement efficiency, shortening a measurement time, and the like can be expected. In addition, by being able to reduce the range of the detection unit t and the control unit c, the chip 10 can be made smaller.

Figure 4:
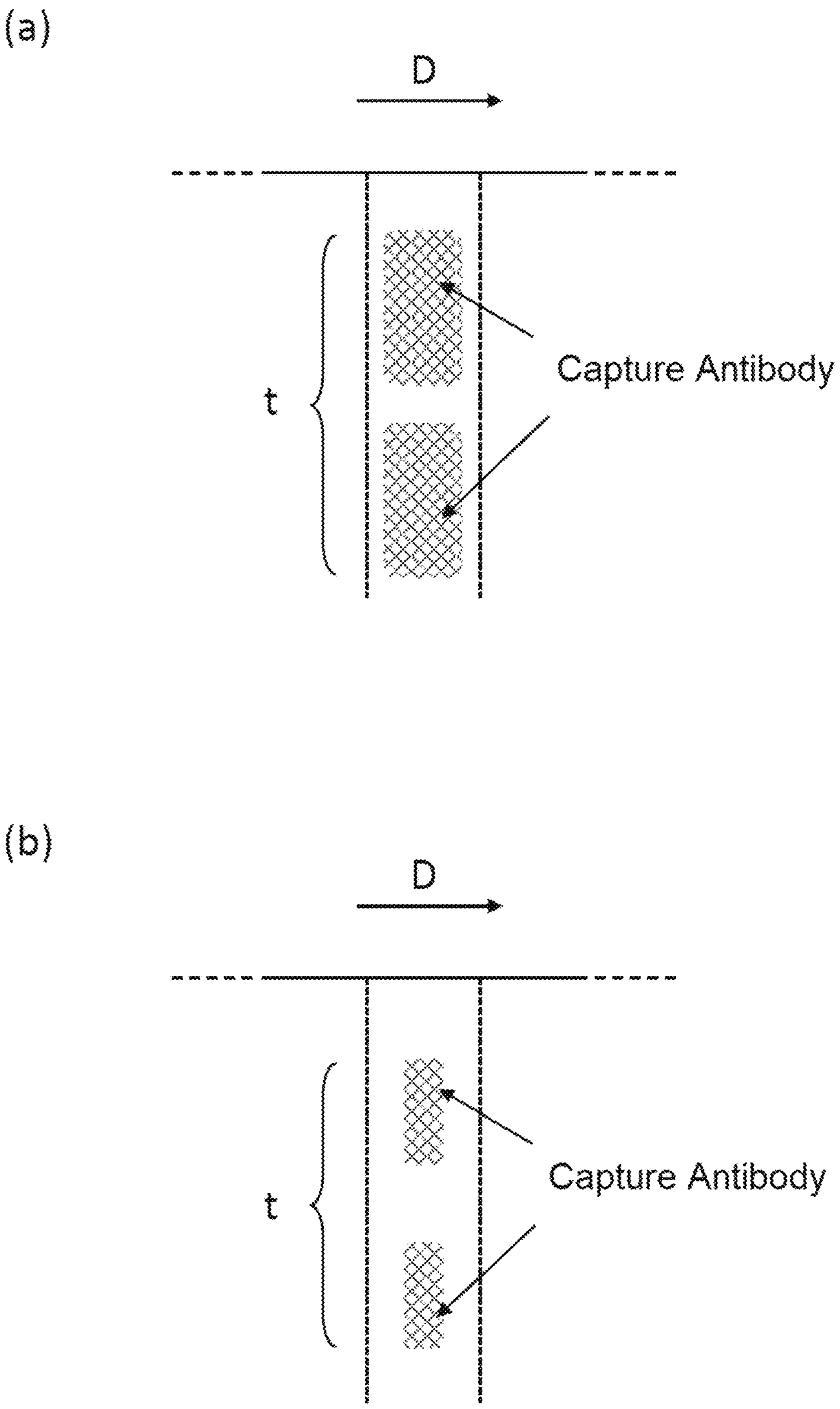
FIG. 4 is a schematic plan view showing examples of aspects of a detection unit of the immunochromatography chip shown in FIGS. 1 and 2; (a) is an aspect in which a capture antibody is immobilized at intervals, and (b) is an aspect in which a range over which a capture antibody is immobilized is smaller than that of the aspect shown in (a).

Further, it should be noted that for the chip 10 that can be used in the method of the present invention, a modality in which the capture antibody and the control antibody are immobilized is not limited to a continuous line. Specifically, the capture antibody and the control antibody may be immobilized at intervals and in parallel to a shorter edge of the carrier 4 of the chip 10. FIG. 4(*a*) is a diagram schematically showing a case in which the detection unit t of the chip 10 shown in FIGS. 1 and 2 is this aspect. FIG. 4(*a*) shows an aspect in which the capture antibodies are immobilized in two lines, and a region in which these capture antibodies are present is the detection unit t, in other words, it shows an aspect in which the detection unit t is configured from two lines along which the capture antibodies are immobilized. The same effects as those described with reference to FIG. 3(*b*) can also be obtained in this aspect. In addition, as shown in FIG. 4(*b*), the capture antibody may be immobilized in a smaller range than that of the aspect shown in FIG. 4(*a*), as long as it is large enough to allow the presence or absence of color development due to the accumulation of the labeling substance to be identified by visual observation.

Further, allowing the capture antibody and the control antibody to be arranged (immobilized) on the immunochromatography chip at intervals also means that multiple kinds of the capture antibodies and the control antibodies can be used. In other words, in one aspect of the chip 10 that can be used in the method of the present invention, the multiple kinds of the capture antibodies are immobilized at intervals on the detection unit t of the carrier 4, and the multiple kinds of the control antibodies are immobilized at intervals on the control unit c of the carrier 4. In this aspect, the multiple kinds of the capture antibodies and the multiple kinds of the control antibodies may be respectively immobilized in line and in parallel to the shorter edge of the carrier 4 of the chip 10, or they may be immobilized so as to be offset upstream or downstream to a development direction D for each kind.

Figure 5:
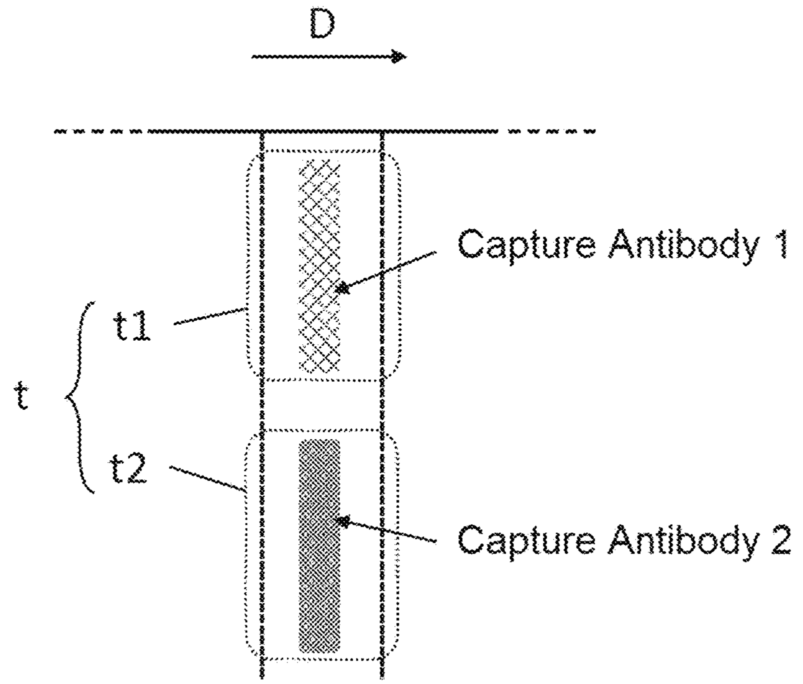
FIG. 5 is a schematic plan view showing examples of aspects of a detection unit of the immunochromatography chip shown in FIGS. 1 and 2; (a) is an aspect in which two kinds of capture antibodies are immobilized in lines, with the capture antibodies immobilized in line and in parallel in a direction perpendicular to a development direction, and (b) is an aspect in which two kinds of capture antibodies are immobilized in a line, with one capture antibody immobilized so as to be offset downstream of another capture antibody.
Figure 5:
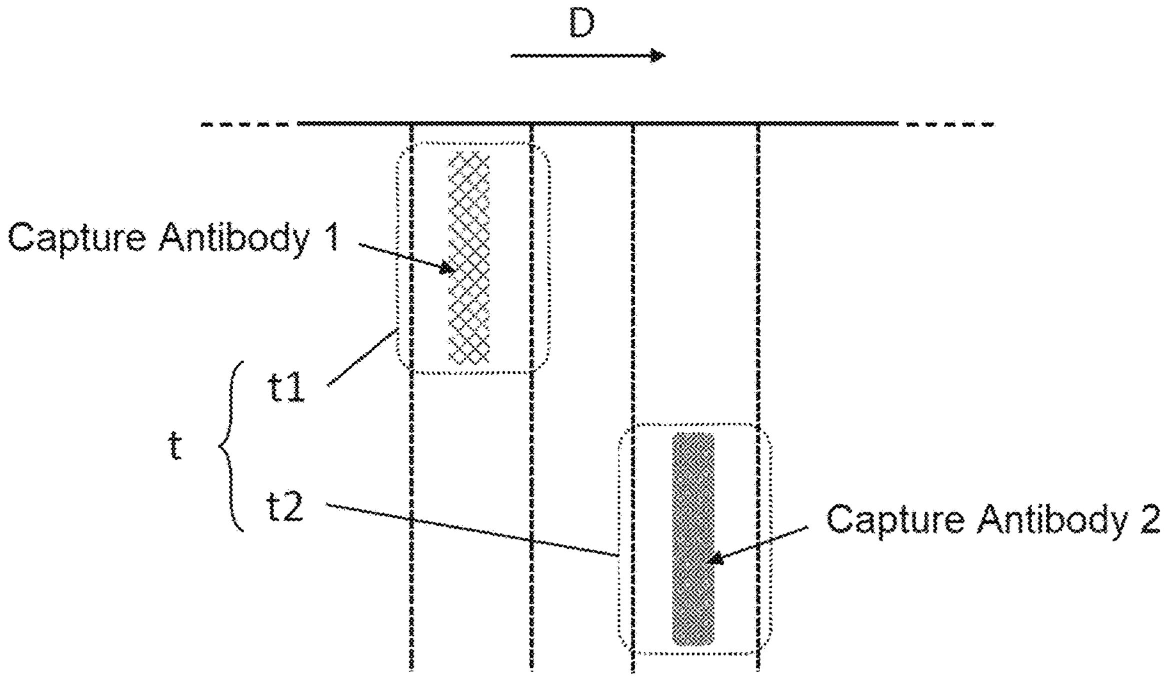

FIGS. 5(*a*) and 5(*b*) are diagrams schematically showing a case in which the detection unit t of the chip 10 shown in FIGS. 1 and 2 is the above aspect. In the aspect shown in FIG. 5(*a*), two kinds of the capture antibodies (a capture antibody 1 and a capture antibody 2) are each immobilized in a line, and the capture antibody 1 and the capture antibody 2 are immobilized in parallel in a direction perpendicular to the development direction D. Also, a region in which the capture antibody 1 is present is a detection unit t1, a region in which the capture antibody 2 is present is a detection unit t2, and the detection unit t1 and the detection unit t2 form the detection unit t. In the aspect shown in FIG. 5(*b*), the two kinds of the capture antibodies (the capture antibody 1 and the capture antibody 2) are each immobilized in a line, with the capture antibody 2 immobilized so as to be offset downstream of the capture antibody 1 in the development direction D. Also, the region in which the capture antibody 1 is present is the detection unit t1, the region in which the capture antibody 2 is present is the detection unit t2, and the detection unit t1 and the detection unit t2 form the detection unit t. Note that while FIGS. 5(*a*) and 5(*b*) show aspects in which there are two kinds of the capture antibodies, it is also possible to immobilize three or more kinds of the capture antibodies on a single chip. According to the chip 10 of the aspects as exemplified in FIGS. 5(*a*) and 5(*b*), multiple kinds of object to be detected can be detected by immunochromatography from a single specimen, and the labeling substance for labeling the object to be detected can be quantified by identification using the electron microscope.

Figure 6:
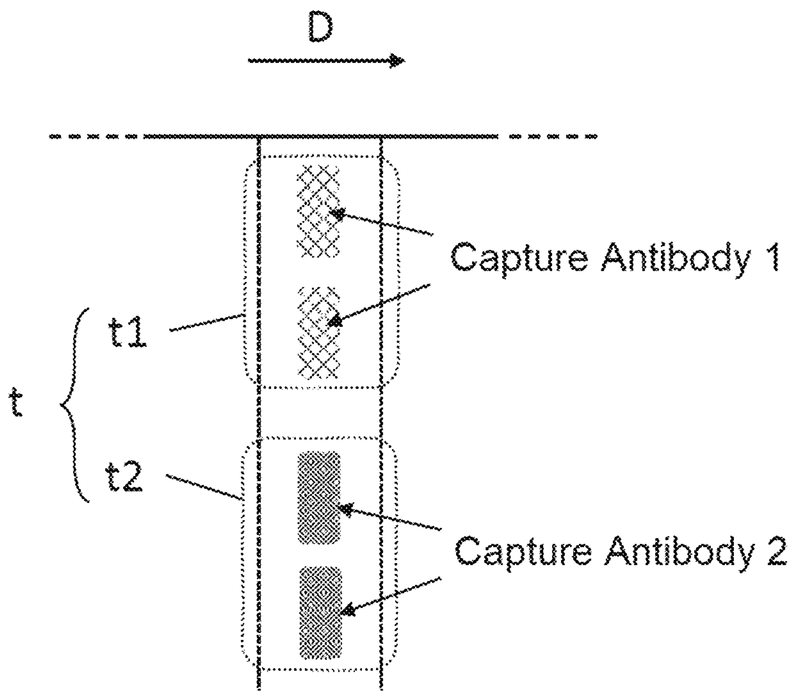
FIG. 6 is a schematic plan view showing examples of aspects of a detection unit of the immunochromatography chip shown in FIGS. 1 and 2; (a) is an aspect in which two kinds of capture antibodies are immobilized at intervals, with the capture antibodies immobilized in line and in parallel in a direction perpendicular to a development direction, and (b) is an aspect in which two kinds of capture antibodies are immobilized at intervals, with one capture antibody immobilized so as to be offset downstream of another capture antibody.
Figure 6:
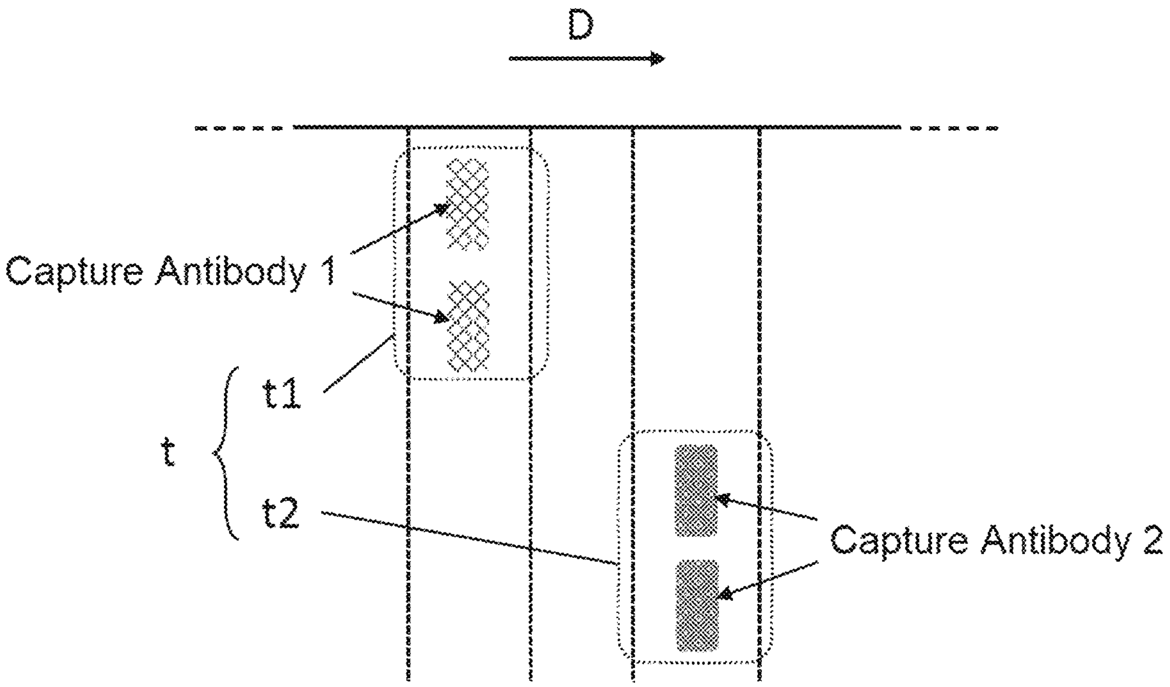

FIGS. 6(*a*) and 6(*b*) are illustrations schematically showing aspects in which a capture antibody 1 and a capture antibody 2 are immobilized at intervals, respectively, in the aspects shown in FIGS. 5(*a*) and 5(*b*). In the aspect shown in FIG. 6(*a*), two kinds of the capture antibodies (the capture antibody 1 and the capture antibody 2) are each immobilized in two lines, with the capture antibody 1 and the capture antibody 2 immobilized in parallel in a direction perpendicular to the development direction D. Also, the region in which the capture antibody 1 is present is the detection unit t1, the region in which the capture antibody 2 is present is the detection unit t2, and the detection unit t1 and the detection unit t2 form the detection unit t. In the aspect shown in FIG. 6(*b*), the two kinds of capture antibodies (the capture antibody 1 and the capture antibody 2) are each immobilized in two lines, with the capture antibody 2 immobilized so as to be offset downstream of the capture antibody 1 in the development direction D. Also, the region in which the capture antibody 1 is present is the detection unit t1, the region in which the capture antibody 2 is present is the detection unit t2, and the detection unit t1 and the detection unit t2 form the detection unit t. Further, while FIGS. 6(*a*) and 6(*b*) show aspects in which there are two kinds of capture antibodies, it is also possible to immobilize three or more kinds of the capture antibodies on a single chip. According to the chip 10 of the aspects as exemplified in FIGS. 6(*a*) and 6(*b*), multiple kinds of object to be detected can be detected by immunochromatography from a single specimen, and the labeling substance for labeling the object to be detected can be quantified by identification using the electron microscope.

For example, a method of applying a minute amount of (fine) fL (femtoliter) or pL (picoliter) order droplets can be applied as a method of arranging the capture antibody and the control antibody on the carrier 4 at intervals. More specifically, examples include a method of applying droplets by attaching them to an outer periphery of an application needle, a method of applying by ejecting a jet flow from a nozzle tip using electrostatic force, and the like.

Further, the chip 10 that can be used in the method of the present invention can be configured so as to be provided with the detection unit dedicated to electron microscope measurement separately from the detection unit for visual observation. A specific aspect of the immunochromatography chip of the present invention (hereinafter simply also referred to as the "chip of the present invention") will be described below with reference to FIGS. 7(*a*) and 7(*b*), as well as FIGS. 8(*a*) and 8(*b*).

Figure 7:
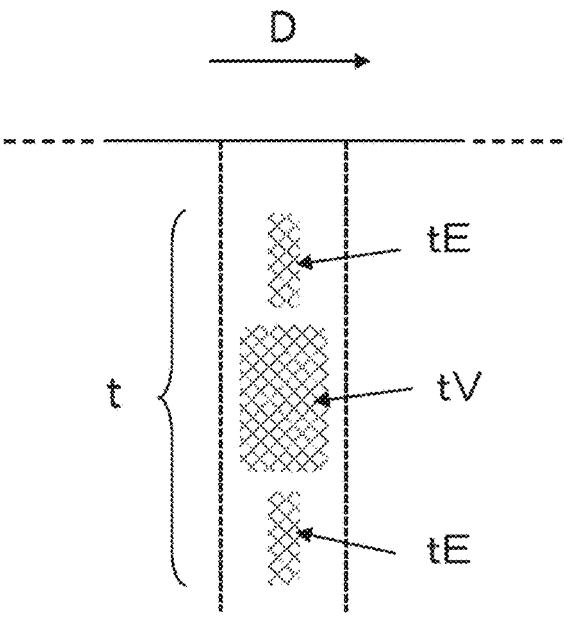
FIG. 7 is a schematic plan view showing an example of a configuration of a chip of the present invention; (a) is an aspect in which detection units dedicated to electron microscope measurement are arranged on both sides of a detection unit for visual observation, and (b) is an aspect in which detection units dedicated to electron microscope measurement are arranged upstream of the detection unit for visual observation.
Figure 7:
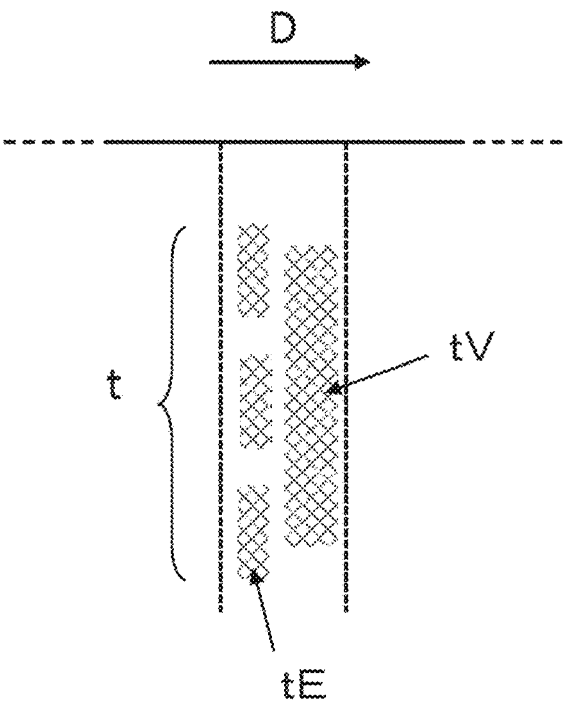

In an aspect shown in FIG. 7(*a*), two detection units tE dedicated to electron microscope measurement are arranged in a line on either side of a detection unit tV for visual observation (a vertical direction of the paper plane of FIG. 7(*a*)), with the capture antibodies immobilized on each of the detection unit tV and the detection units tE. In FIG. 7(*a*), while the detection unit tV has a roughly rectangular shape, it is not limited to this shape as long as it is large enough to allow the presence or absence of color development due to the accumulation of the labeling substance to be identified by visual observation. The same applies to the later-described FIGS. 7(*b*), 8(*a*), and 8(*b*).

Note that a quantity of detection units tE is preferably two or more, and more preferably three or more, from the viewpoint of further ensuring precision in electron microscope measurement. In other words, in the chip of the present invention, it is possible to ensure precision in electron microscope measurement even when the quantity of the detection units tE is three or less.

Further, in FIG. 7(*a*), while a line of the detection units tE is shown as a constant size for the sake of clarity, a size of the detection units tE may be smaller than that of the detection unit tV. In other words, for the chip of the present invention, since an arrangement of the detection unit tV and the detection unit tE is known in advance, it is possible to perform a two-step detection which involves, as a first step, performing a simple screening by confirming color development originating from the labeling substance for labeling the object to be detected on the detection unit tV by visual observation, then, as a second step, quantifying by measuring a quantity of the labeling substances on the detection unit tE by performing measurement by electron microscope. In other words, in the chip of the present invention, since highly magnified and high-resolution images are obtained in the detection unit tE under measurement conditions by electron microscope, the detection unit tV may be at a degree capable of confirming the presence or absence of color development originating from the labeling substance. According to the chip of the present invention having this kind of configuration, not only can the same effect as is described with reference to FIG. 3(*b*) be obtained, but the amount of the capture antibody used can also be reduced to less than that of the aspect shown in FIG. 3(*b*), thus further effects can be expected.

In an aspect shown in FIG. 7(*b*), three detection units tE dedicated to electron microscope measurement are arranged in a line at intervals upstream of a detection unit tV for visual observation, with capture antibodies immobilized on each of the detection unit tV and the detection units tE. As is described above with respect to FIG. 7(*a*), since the size of the detection units tE may be smaller than that of the detection unit tV, when confirming the presence or absence of color development originating from the labeling substance on the detection unit tV by visual observation, any impact due to an arrangement of the detection units tE upstream of the detection unit tV can be ignored.

Figure 8:
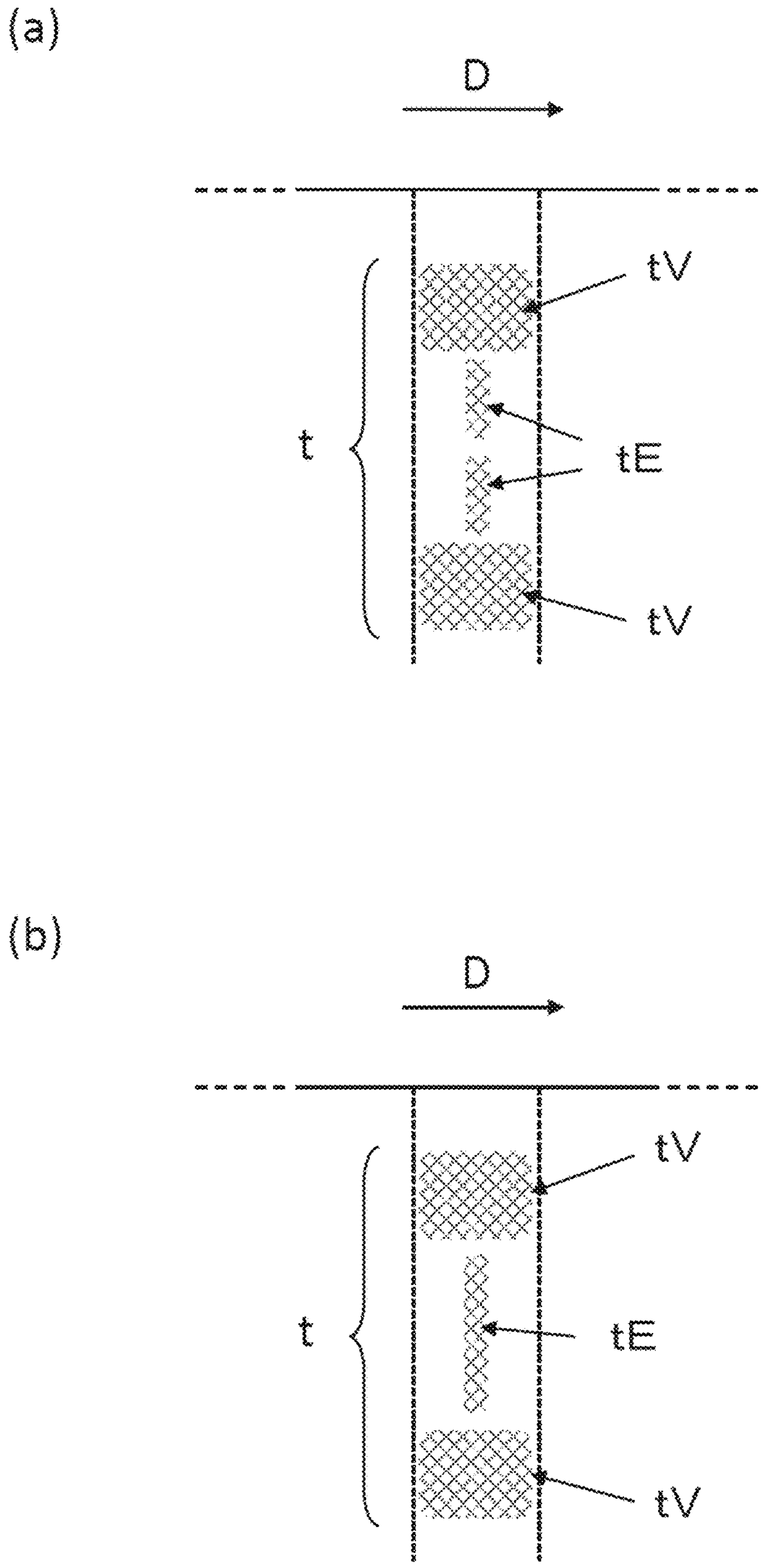
FIG. 8 is a schematic plan view showing an example of a configuration of a chip of the present invention; (a) is an aspect in which detection units for visual observation are arranged on both sides of detection units dedicated to electron microscope measurement; and (b) is an aspect in which a detection unit dedicated to electron microscope measurement in the aspect shown in (a) is in a continuous line.

In an aspect shown in FIG. 8(*a*), two detection units tE dedicated to electron microscope measurement are arranged in a line at intervals, detection units tV for visual observation are arranged on either side of the detection units tE (a vertical direction of the paper plane of FIG. 8(*a*)), and capture antibodies are immobilized on each of the detection units tV and the detection units tE. FIG. 8(*b*) shows an aspect in which a detection unit tE is in a continuous line in the aspect shown in FIG. 8(*a*).

The same effects as those described with reference to FIG. 7(*a*) can also be obtained in the above-described aspects shown in FIGS. 7(*b*), 8(*a*), and 8(*b*). Note that the aspects shown in FIGS. 7(*a*) and 7(*b*), as well as FIGS. 8(*a*) and 8(*b*), are for exemplifying specific aspects of the chip of the present invention and are not intended to limit the invention to specific aspects. In addition, while it is not shown in FIGS. 7(*a*) and 7(*b*), as well as FIGS. 8(*a*) and 8(*b*), the aspect of the control unit c is not particularly limited, and the control unit c may be used for visual observation as is described above with respect to the detection unit t, or it may be dedicated to electron microscope measurement. An aspect in which the control unit c is for visual inspection has an advantage in that the detection unit t can be subjected to measurement by electron microscope after visually confirming color development of the control unit c due to development of the specimen. On the other hand, an aspect in which the control unit c is dedicated to electron microscope measurement has an advantage in that the step of visually confirming the presence or absence of color development due to the accumulation of the labeling substance can be omitted, and by subjecting both the detection unit t and the control unit c to measurement by electron microscope, the results of immunochromatography can be quantified quickly and more easily.

Further, in another aspect of the chip of the present invention, a configuration in which only a detection unit dedicated to electron microscope measurement is provided is also possible. In other words, in the present aspect, the chip of the present invention is not provided with any detection un its other than the detection unit dedicated to electron microscope measurement (such as a detection unit for visual observation).

Figure 9:
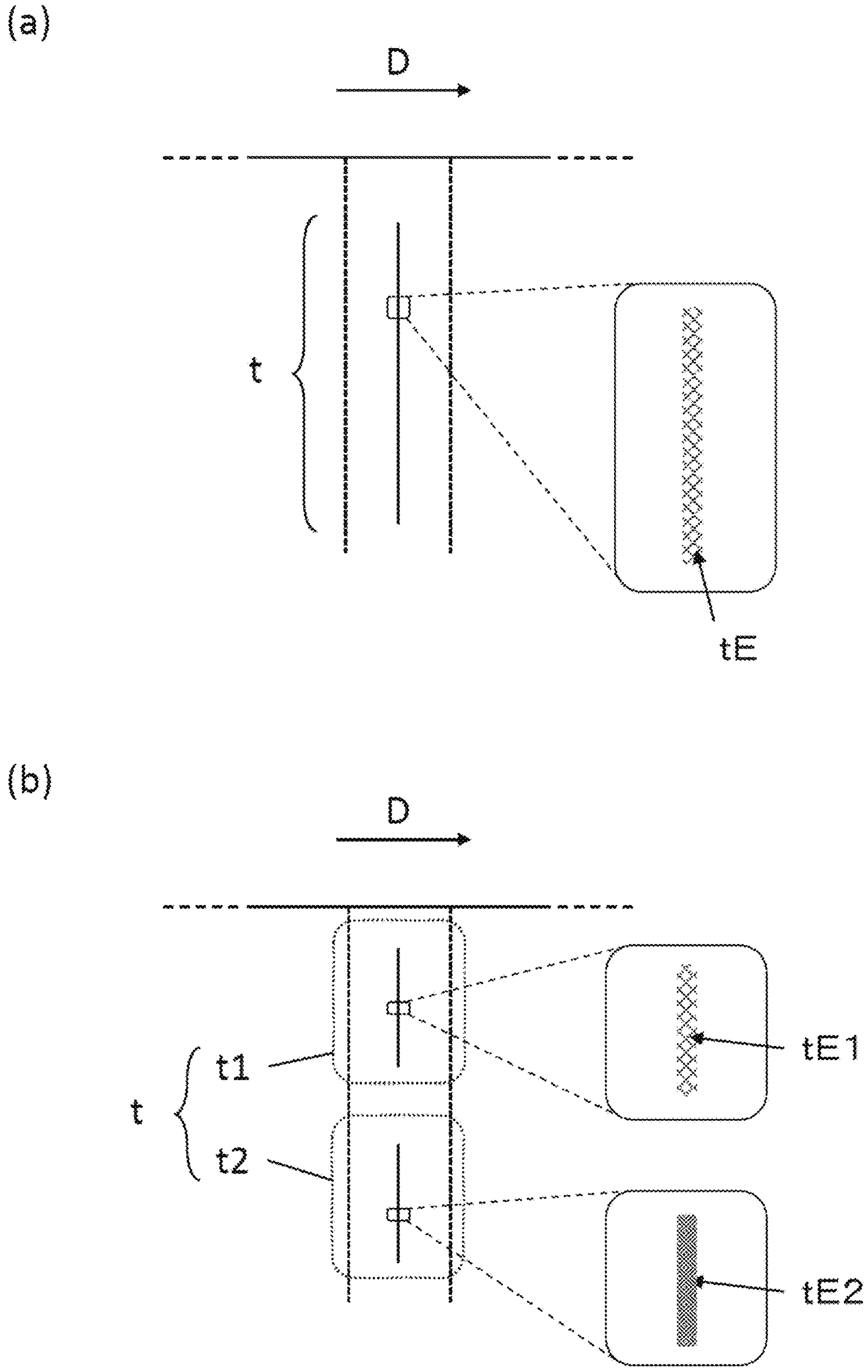
FIG. 9 is a schematic plan view showing an example of a configuration of a chip of the present invention; (a) is an aspect in which a detection unit dedicated to electron microscope measurement is arranged in a continuous line, and (b) is an aspect in which two detection units dedicated to electron microscope measurement are arranged in a continuous line, and different kinds of capture antibodies are immobilized.

FIGS. 9(*a*) and 9(*b*) are illustrations schematically showing a case in which the chip of the present invention is the above aspect. In an aspect shown in FIG. 9(*a*), detection units tE dedicated to electron microscope measurement are arranged in a continuous line, and these detection units tE form a detection unit t. In an aspect shown in FIG. 9(*b*), different kinds of capture antibodies are immobilized on a detection unit tE1 and a detection unit tE2 dedicated to electron microscope measurement, and the detection unit tE1 and the detection unit tE2 form the detection unit t. Note that in FIGS. 9(*a*) and 9(*b*), the detection unit tE, the detection unit tE1, and the detection unit tE2 forming each detection unit t are shown as solid lines, and a portion thereof is shown as an enlarged view on the right side for the sake of clarity. In FIGS. 9(*a*) and 9(*b*), the detection unit tE, the detection unit tE1, and the detection unit tE2 are in a continuous line, however they may be in a line spaced apart in intervals. Further, while it is not shown in FIGS. 9(*a*) and 9(*b*), the aspect of the control unit c is not particularly limited, and the control unit c may be used for visual observation as is described above, or it may be dedicated to electron microscope measurement. Among these, since by setting the control unit c to be dedicated to electron microscope measurement, the step of visually confirming the presence or absence of color development due to the accumulation of the labeling substance can be omitted, and by subjecting both the detection unit t and the control unit c to measurement by electron microscope, the results of immunochromatography can be quantified quickly and more easily, it is preferable.

[Application of Auxiliary Liquid]

In the method of the present invention, a timing of applying the auxiliary liquid is not particularly limited. For example, in the method of the present invention, the specimen and the auxiliary liquid can be applied simultaneously. More specifically, the specimen and the auxiliary liquid may be simultaneously dropped onto the specimen pad 2 of the chip 10. Note that in this case, the auxiliary liquid may be dropped on the specimen pad 2 immediately after the specimen is dropped on the specimen pad 2, or the auxiliary liquid may be dropped on the specimen pad 2 after the specimen has been dropped on the specimen pad 2 and before the color development of the control unit c of the carrier 4 has been visually confirmed by the development of the specimen. In other words, in the present description, "simultaneously" with respect to the application of the specimen and the auxiliary liquid refer to the application of the auxiliary liquid is performed from a point in time at which the specimen is dropped on the specimen pad 2 of the chip 10 and to before the color development of the control unit c of the carrier 4 has been visually confirmed.

In addition, in the method of the present invention, the auxiliary liquid can be developed after the development of the specimen. More specifically, the auxiliary liquid may be dropped on the specimen pad 2 after the specimen has been dropped on the specimen pad 2 of the chip 10 and the color development of the control unit c of the carrier 4 has been visually confirmed by the development of the specimen. Alternatively, the auxiliary liquid may be applied to the detection unit t of the carrier 4 after the specimen has been dropped on the specimen pad 2 of the chip 10 and the color development of the control unit c of the carrier 4 has been visually confirmed by the development of the specimen. When the auxiliary liquid is applied to the detection unit t of the carrier 4, an application means of the auxiliary liquid is not particularly limited, however it is desirable to apply it without directly contacting the detection unit t of the carrier 4. For example, a generally used pipettor may be used, or an application device or the like capable of controlling a droplet amount may be used. Note that when the transparent film or the like is applied to the upper surface of the carrier 4, the auxiliary liquid is applied with the film or the like in a state of having been removed.

In addition, in the method of the present invention, the auxiliary liquid can also be applied before the specimen is developed. In one form of the present aspect, the specimen is dropped on the specimen pad 2 after the auxiliary liquid has been dropped on the specimen pad 2 of the chip 10 and the auxiliary liquid has been left to develop for a predetermined time. Alternatively, in another form of the present aspect, the auxiliary liquid is applied to the detection unit t of the chip 10 in advance, and with the auxiliary liquid in a dried state, the specimen is dropped on the specimen pad 2. Moreover, the above aspect may be combined with the above-described aspect in which the specimen and the auxiliary liquid are simultaneously applied, or the aspect in which the auxiliary liquid is developed after the development of the specimen.

[Measurement by Electron Microscope]

The immunochromatography chip to which the auxiliary liquid for immunochromatography measurement is applied as is described above is subjected to measurement by electron microscope. Specifically, the detection unit t of the carrier 4 of the chip 10 is subjected to measurement by electron microscope. At this time, the detection unit t (that is, a material forming the carrier, for example, the nitrocellulose membrane) and the complex of the object to be detected and the labeled antibody in the specimen captured by the capture antibody immobilized on the detection unit t (that is, an antigen-antibody reaction product composed of a capture antibody-object to be detected-labeled antibody) are in a state in which the auxiliary liquid is applied, in other words, the detection unit t and the antigen-antibody reaction product are in a state of being exposed to the auxiliary liquid.

The detailed mechanism by which the application of the auxiliary liquid improves the sharpness of the electron microscope images (contributes to the sharpness of the images) is not necessarily clear, however the present inventors believe that when the detection unit t is irradiated with an electron beam in the state in which the detection unit t and the above antigen-antibody reaction product are exposed to the auxiliary liquid under measurement conditions by electron microscope, a thin membrane is formed on a surface of the detection unit t, as well as the antigen-antibody reaction product, and conductivity is imparted all over the detection unit t (the nitrocellulose membrane) and the antigen-antibody reaction product. Also, it is believed that since energy from the electron beam irradiated to the detection unit t is dispersed, charging (charge-up) and heat generation of the antigen-antibody reaction product are suppressed, and further, moisture contained in the nitrocellulose membrane and the antigen-antibody reaction product is retained. As a result, in the electron microscope images, the contrast between the background carrier (cellulose fibers of the nitrocellulose membrane) and the target object to be detected is clear, and the labeling substance (for example, gold nanoparticles, platinum-gold nanoparticles, and the like) of the object to be detected can be identified as clear (well-defined) particles. Also, by measuring the quantity of these labeling substances, the results of immunochromatography can be easily quantified in a short time.

The quantity of the labeling substances can be measured by visual observation. This is specifically demonstrated in the below-described examples. In addition, the quantity of the labeling substances can be measured by an image recognition system using machine learning or deep learning, and it is also possible to use an automatic analysis system to identify the object to be detected by identifying the labeling substance of the object to be detected in the images using artificial intelligence (AI). Further, it is also possible to identify the object to be detected by combining scanning electron microscopy (SEM) or transmission electron microscopy (TEM) with energy dispersive X-ray spectroscopy (EDX) to identify the labeling substances of the object to be detected in the images using EDX.

<Immunochromatography Measurement Kit>

The immunochromatography measurement kit of the present invention (hereinafter simply also referred to as the "kit of the present invention") includes the auxiliary liquid for immunochromatography measurement as a constituent element.

In the kit of the present invention, those described above with respect to the method of the present invention can be used as the above auxiliary liquid. Since the characteristics and specific composition of the auxiliary liquid are as is described above, a detailed description thereof has been omitted.

In one aspect of the kit of the present invention, a liquid for preparing the specimen (a specimen extract liquid) or the like may be included in the constituent element separately from the above auxiliary liquid. In other words, in the present aspect, a user can perform measurement by electron microscope by applying the auxiliary liquid after preparing the specimen using the specimen extract liquid or the like included in the kit of the present invention.

The kit of the present invention may further include the immunochromatography chip as a constituent element in addition to the above auxiliary liquid. The immunochromatography chip that can be used in the kit of the present invention is not particularly limited, as long as it is a chip that can be used for ordinary immunochromatography. For example, the chip 10 described in relation to the method of the present invention with reference to FIGS. 1 and 2 can be used. In addition, the immunochromatography chip may be the chip of the present invention described with reference to FIGS. 7(*a*) and 7(*b*), FIGS. 8(*a*) and 8(*b*), as well as FIGS. 9(*a*) and 9(*b*). Since the configurations of the chip 10 and the chip of the present invention are as is described above, a detailed description thereof has been omitted.

The kit of the present invention may include an instruction manual for the above auxiliary liquid as a constituent element. Examples of the instruction manual include, but are not particularly limited to, a package insert, a package label, or an instruction manual, such as, for example, attached documents, prescribing information, and leaflets. The instruction manual may be provided as a paper medium, or it may be provided as a modality such as an electronic medium (for example, a website or an e-mail provided via the Internet).

The embodiments of the present invention will be described in more detail below based on the examples. Note that the scope of the present invention should not be interpreted as being limited by the examples shown below.

EXAMPLES

Measurement Example Using Influenza Virus Antigen Detection Kit

The subjects of detection were measured by immunochromatography under the following conditions and in the following procedure using commercially available Type A and Type B influenza virus antigen detection kits (manufactured by TAUNS).

With the cooperation of the Hamamatsu University Hospital clinical laboratory, two sample kits positive for Type A influenza virus antigens used in actual testing were used as the target to be measured. For these sample kits, the specimen (a specimen liquid prepared from a liquid taken from a patient's pharynx) was developed using chromatography, and the color development of the detection unit of the Type A influenza virus antigen (A line) and the control unit (C line) was in a state able to be confirmed by visual observation.

After an aqueous solution including 1 weight percent of polysorbate 20 as the auxiliary liquid (an aqueous solution with Tween 20 at 1%) was dropped on the specimen pad of one of the sample kits and developed using chromatography, the A line was subjected to SEM measurement (Example 1). In another of the sample kits, the A line was subjected to SEM measurement in its present state without applying the auxiliary liquid (Comparative Example 1). A HITACHI Tabletop Microscope Miniscope (registered trademark) TM4000Plus was used as the SEM.

Figure 10:
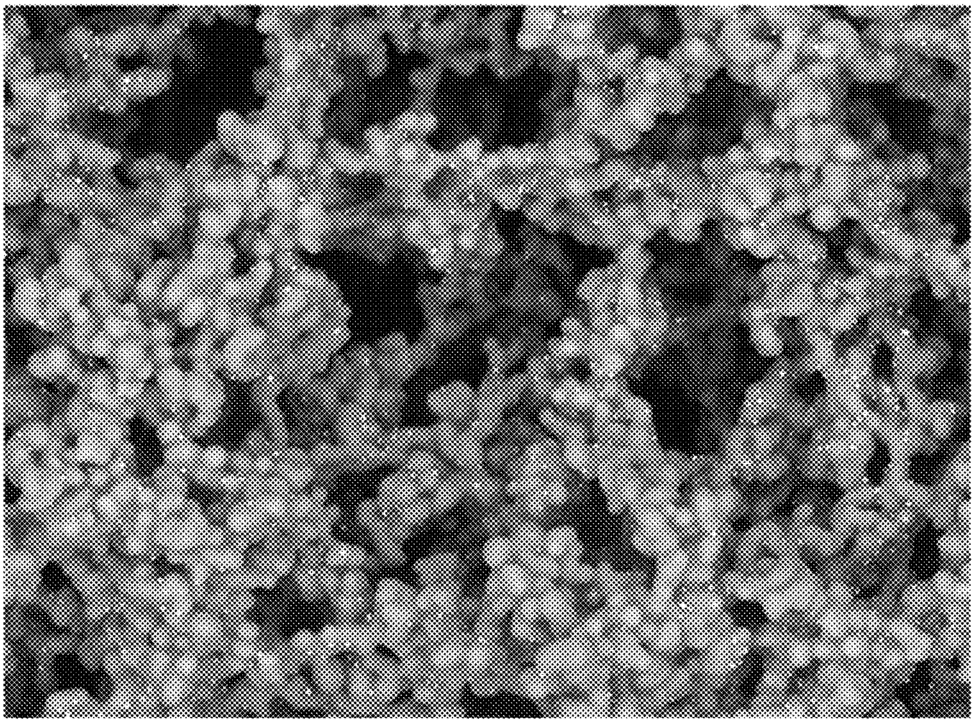
FIG. 10 is a SEM image of a detection unit (line A) for an influenza A virus antigen in which a sample kit positive for the influenza A virus antigen was set as a target to be measured; (a) is Example 1 and (b) is Comparative Example 1.
Figure 10:
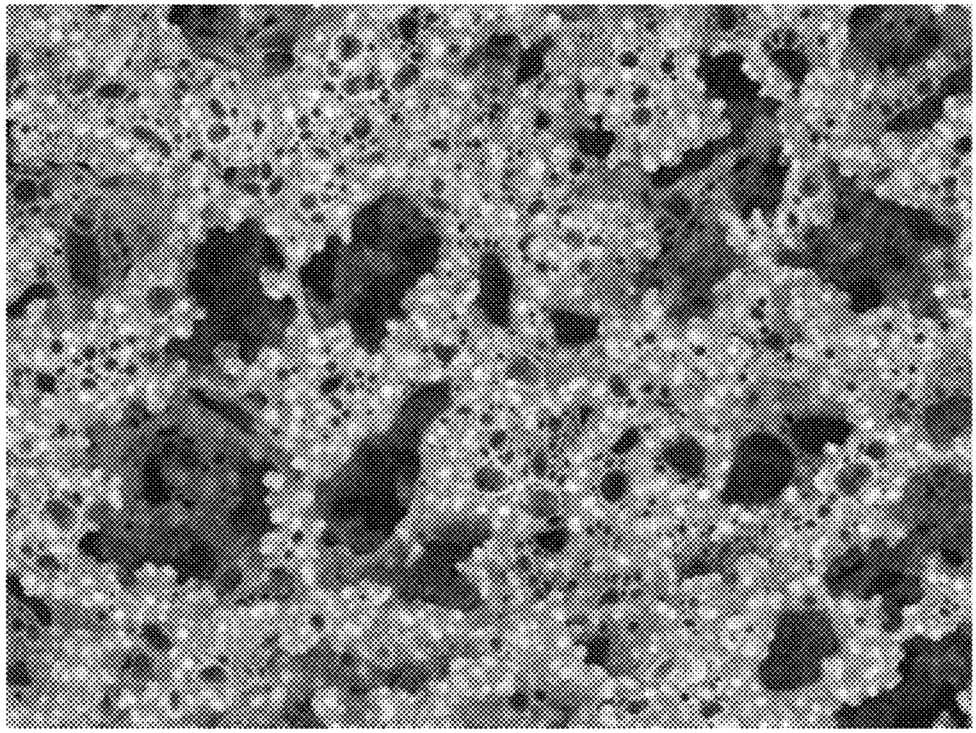

FIG. 10(*a*) is an SEM image of the A line of the sample kit of Example 1, and FIG. 10(*b*) is an SEM image of the A line of the sample kit of Comparative Example 1.

For the sample kit of Example 1 shown in FIG. 10(*a*), the contrast between the background carrier (the cellulose fibers of the nitrocellulose membrane) and the labeling substance (the platinum-gold nanoparticles) of the labeled antibody bound to the influenza virus is clear, and the platinum-gold nanoparticles can be confirmed as clear (well-defined) particles. In addition, an outer shape of the background cellulose fibers can be clearly confirmed. This suggests that by applying not only the antigen-antibody reaction product formed on the A line, but also the auxiliary liquid to the carrier, and more specifically, by developing the auxiliary liquid with chromatography through the A line (the detection unit), impurities contained in the nitrocellulose membrane forming the carrier were flushed downstream together with the auxiliary liquid, in other words, the nitrocellulose membrane of the carrier was washed by the auxiliary liquid.

On the other hand, for the sample kit of Comparative Example 1 shown in FIG. 10(*b*), structural changes, such as bubbles (bubbles or foam), occur in a background cellulose fiber portion, thus it is difficult to distinguish the platinum-gold nanoparticles, which are the labeling substance of the influenza virus. It should be mentioned that in actual SEM measurement, since the electron beam is continuously irradiated from the electron source, the above-described structural change of the cellulose fiber portion also occurs continuously, thus it would be more difficult to identify the platinum-gold nanoparticles of the labeling substance and measure the quantity thereof than it is in the still image shown in FIG. 10(*b*).

These results demonstrate that the labeling substances for labeling the object to be detected in the specimen can be identified at a high magnification and a high resolution using an electron microscope by the method of the present invention, and the results of immunochromatography can be easily quantified in a short time by measuring the quantity of the labeling substances.

Next, with the cooperation of the Hamamatsu University Hospital clinical laboratory, 197 sample kits used in actual testing were used as the target to be measured. For these sample kits, the specimen (a specimen liquid prepared from a liquid taken from a patient's pharynx) was developed using chromatography, and the color development of the control unit (the C line) of the carrier was in a state able to be confirmed by visual observation. After an aqueous solution including 1 weight percent of polysorbate 20 as the auxiliary liquid (an aqueous solution with Tween 20 at 1%) was dropped on the specimen pads of each sample kit and developed using chromatography, the detection units of Type A and Type B influenza virus antigens (the A line and the B line, respectively) and a background unit (any portion of the carrier excluding the A line, the B line, and the C line) were subjected to SEM measurement.

The equipment, measurement conditions, and determination criteria used for the above measurement are as follows:

[Equipment and Measurement Conditions]

- Scanning electron microscope: HITACHI Tabletop Microscope Miniscope (registered trademark) TM4000Plus
- Voltage: 10 kV, Mode 3 or 4
- Measurement magnification: 1000 to 1200 times
- Imaging mode: reflected electron mode

[Determination Criteria]

- First, six fields of view are arbitrarily selected from the background unit, the quantity of the platinum-gold nanoparticles in each field of view is measured, and an average value per field of view is calculated.
- Next, six fields of view are arbitrarily selected from the A line and the B line, the quantity of the platinum-gold nanoparticles in each field of view is measured, and an average value per field of view is calculated. When the average value is 5 or more, the sample is determined to be positive, and the following t-test is performed.
- The average value of the A line and/or the B line determined to be positive above is compared with the average value obtained for the background unit, and a sample having a p value of $p<0.01$ or less by t-test is determined to be "positive".

For the measurement sites (measurement positions) of the A line and the B line, a site in which the boundary line upstream of the C line was located in the center of the field of view was set as a reference (position 0), a site 3.8 to 3.9 mm upstream from the position 0 was set as the B line measurement site, and a site 6.8 to 6.9 mm from the position 0 was set as the A line measurement site. Note that since the platinum-gold nanoparticles may be detected in cellulose fibers other than those of each line (a background signal), as a preliminary experiment, when a frequency of the background signal was compared upstream of the A line measurement site, between the A line measurement site and the B line measurement site, and between the B line measurement site and the position zero, the results were almost the same. Therefore, an arbitrary site has been selected from these portions as the measurement site of the background unit.

Figure 11:
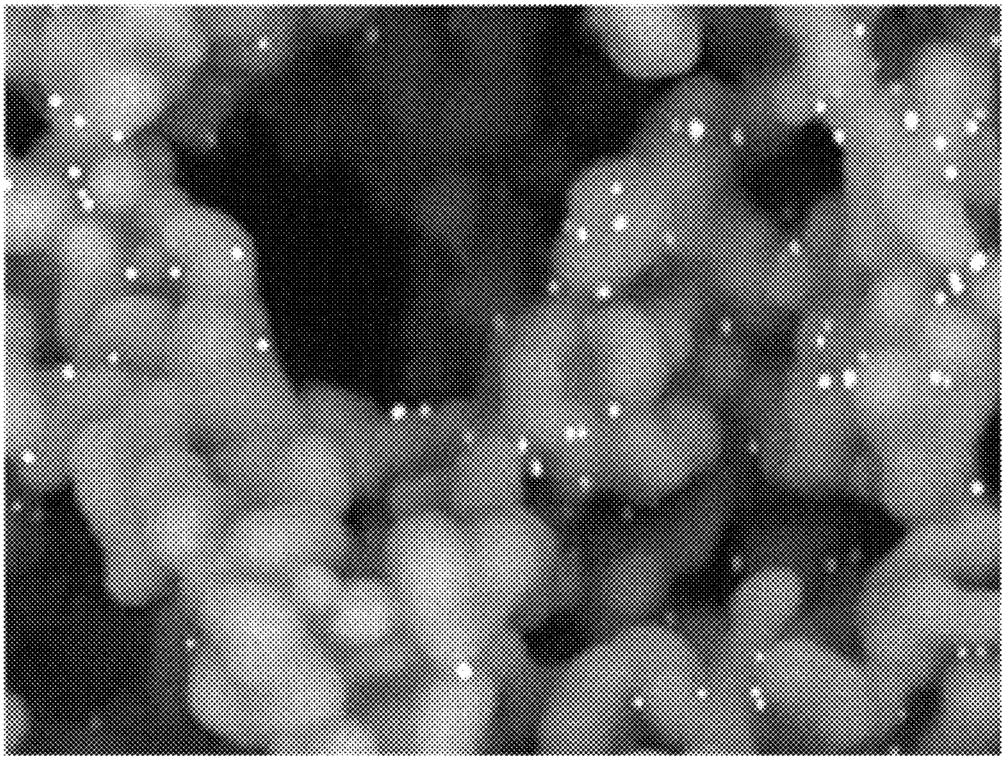
FIG. 11(*a*) is an example of an SEM image of a detection unit (test line) determined as positive according to measurement conditions and determination criteria described in the examples, and (b) is an example of a SEM image of a background unit.
Figure 11:
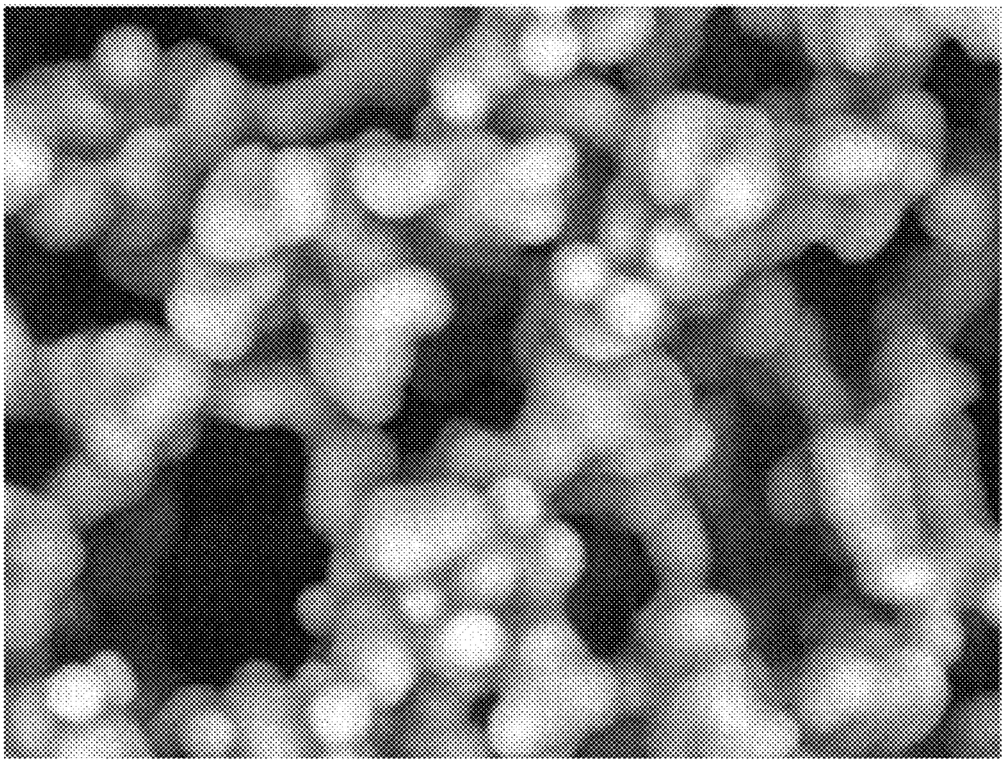

FIG. 11(*a*) is an example of an SEM image of the detection unit (test line) determined to be positive according to the above measurement conditions and determination criteria. In FIG. 11(*a*), bright particles are the platinum-gold nanoparticles. As shown in FIG. 11(*a*), since the contrast between the platinum-gold nanoparticles and the cellulose fiber is clear, a quantity of the platinum-gold nanoparticles can be measured by visual observation. FIG. 11(*b*) is an example of an SEM image of the background unit. As shown in FIG. 11(*b*), since the outer shape of the cellulose fibers is clear, a presence or absence of the platinum-gold nanoparticles in the background unit can also be clearly determined.

As a result of measuring a total of 197 sample kits as described above, whereas in the conventional qualitative determination by visual observation, 25 cases/197 cases (12.7%) of the A line were determined to be positive and 0 cases/197 cases (0%) of the B line were determined to be positive, in the quantitative determination of identifying the labeling substance by visual observation using an electron microscope, 31 cases/197 cases (15.7%) of the A line were determined to be positive and 2 cases/197 cases (1.0%) of the B line were determined to be positive. In comparison with rRT-PCR, in a highly sensitive portion with a small viral load at a threshold of (Ct value) $30 \leq Ct \leq 38$, 2/7 cases (28.6%) were determined to be positive with the naked eye, and 5/7 cases (71.4%) were determined to be positive with an electron microscope, thus an overwhelmingly high degree of sensitivity has been achieved. These results show that the method of the present invention can measure the object to be detected with higher sensitivity than the conventional qualitative determination by visual observation, and that the method is capable of making a positive determination with a higher degree of precision.

INDUSTRIAL APPLICABILITY

According to the present invention, since the results of immunochromatography can be easily quantified in a short time, it is possible to remarkably improve accuracy when compared to quantitative performance combined with densitometry developed thus far. In addition, an instability in conventional methods following a sensitization reaction with silver or the like can be overcome, and more accurate and highly sensitive measurement results can be obtained. In particular, since the sensitization reaction is not required in the method of the present invention, an advantage is that any artifacts of the sensitization reaction can be reliably excluded. In addition, more accurate measurement results can be obtained and in a shorter time than conventional PCR methods and ELISA methods.

REFERENCE SIGNS LIST

- 10 Immunochromatography chip
- 2 Specimen pad
- 3 Conjugate pad
- 4 Carrier
- 5 Absorbent pad
- D Development direction
- t, t1, t2 Detection unit
- tV, tV1, tV2 Detection unit for visual observation tE, tE1, tE2 Detection unit dedicated to electron microscope measurement c Control unit

The invention claimed is:

1. An immunochromatography measurement method, comprising:

preparing a specimen and an auxiliary liquid other than the specimen, and performing the measurement, wherein the performing the measurement consists essentially of applying the specimen and a liquid consisting of the auxiliary liquid to an immunochromatography chip, and measuring the chip by an electron microscope, and wherein the auxiliary liquid consists of:

at least one compound selected from the group consisting of glycerin, a glycerin substitute, polysorbate 20, polysorbate 40, polysorbate 60, polysorbate 65, polysorbate 80, polysorbate 85, and a polysorbate alternative; and optionally at least one compound selected from the group consisting of monosaccharides, disaccharides, salts, and buffer solutions.

2. The method according to claim 1, wherein the auxiliary liquid is provided with conductivity for preventing charging and heat generation, which contributes to a sharpness of images under measurement conditions by the electron microscope.

3. The method according to claim 1, wherein the auxiliary liquid has a property of forming a membrane by polymerization under measurement conditions by the electron microscope.

4. The method according to claim 1, wherein the method is immunochromatography using a labeled antibody supporting metal nanoparticles as a labeling substance, and a capture antibody having a property of binding to a complex of the labeled antibody and an object to be detected in the specimen.

5. The method according to claim 4, wherein the capture antibody is immobilized on the immunochromatography chip at spatial intervals.

6. The method according to claim 1, wherein the specimen and the liquid consisting of the auxiliary liquid are applied simultaneously.

7. The method according to claim 1, wherein the liquid consisting of the auxiliary liquid is developed after the specimen has been developed.

8. The method according to claim 4, wherein the object to be detected is identified by identifying the labeling substance in an electron microscope image using artificial intelligence.

9. The method according to claim 4, wherein the object to be detected is identified by identifying the labeling substance in the electron microscope image using energy dispersive X-ray spectroscopy (EDX).

10. An immunochromatography measurement kit consisting essentially of a liquid consisting of an auxiliary liquid for immunochromatography measurement, and an immunochromatography chip, wherein the immunochromatography chip comprises:

a specimen pad to which a specimen and the auxiliary liquid can be applied; and a carrier comprising a detection unit dedicated to electron microscope measurement, and wherein the auxiliary liquid consists of:

at least one compound selected from the group consisting of glycerin, a glycerin substitute, polysorbate 20, polysorbate 40, polysorbate 60, polysorbate 65, polysorbate 80, polysorbate 85, and a polysorbate alternative; and optionally at least one compound selected from the group consisting of monosaccharides, disaccharides, salts, and buffer solutions, and wherein the auxiliary liquid improves a sharpness of images when measuring an immunochromatography chip by an electron microscope.

11. The immunochromatography measurement kit according to claim 10, wherein the immunochromatography chip further comprises a conjugate pad, a labeled antibody supporting metal nanoparticles as a labeling substance is immobilized at a predetermined position on the conjugate pad, and a capture antibody having a property of binding to a complex of the labeled antibody and an object to be detected is immobilized on the detection unit dedicated to electron microscope measurement.

12. The immunochromatography measurement kit according to claim 11, wherein the capture antibody is immobilized at spatial intervals on the detection unit dedicated to electron microscope measurement.

13. The immunochromatography measurement kit according to claim 10, wherein the carrier in the immunochromatography chip further comprises an additional detection unit for visual observation.

14. The immunochromatography measurement kit according to claim 10, wherein the carrier in the immunochromatography chip does not comprise any additional detection units other than the detection unit dedicated to electron microscope measurement.

15. The method according to claim 1, wherein the immunochromatography chip comprises;

a specimen pad to which the specimen and the auxiliary liquid can be applied; and a carrier comprising a detection unit dedicated to electron microscope measurement.

16. The method according to claim 15, wherein the carrier in the immunochromatography chip does not comprise any additional detection units other than the detection unit dedicated to electron microscope measurement.

17. The method according to claim 15, wherein the immunochromatography chip further comprises an absorbent pad arranged on a downstream side of the carrier.

18. The immunochromatography measurement kit according to claim 10, wherein the immunochromatography chip further comprises an absorbent pad arranged on a downstream side of the carrier.

* * * * *